(12) United States Patent
Nakata

(10) Patent No.: US 10,820,961 B2
(45) Date of Patent: Nov. 3, 2020

(54) SURGICAL MICROSCOPE SYSTEM HAVING HORIZONTAL AND VERTICAL SLIDERS

(71) Applicant: MITAKA KOHKI CO., LTD., Tokyo (JP)

(72) Inventor: Yusuke Nakata, Tokyo (JP)

(73) Assignee: MITAKA KOHKI CO., LTD., Tokyo (JP)

( * ) Notice: Subject to any disclaimer, the term of this patent is extended or adjusted under 35 U.S.C. 154(b) by 138 days.

(21) Appl. No.: 16/172,090

(22) Filed: Oct. 26, 2018

(65) Prior Publication Data

US 2019/0125481 A1 May 2, 2019

(30) Foreign Application Priority Data

Oct. 30, 2017 (JP) .................. 2017-208797

(51) Int. Cl.
*A61B 90/25* (2016.01)
*A61B 90/50* (2016.01)
*G02B 21/00* (2006.01)
*G02B 21/24* (2006.01)
*G02B 7/00* (2006.01)

(52) U.S. Cl.
CPC ............. *A61B 90/25* (2016.02); *A61B 90/50* (2016.02); *G02B 21/0012* (2013.01); *G02B 21/248* (2013.01); *A61B 2090/504* (2016.02); *G02B 7/001* (2013.01); *G02B 21/24* (2013.01)

(58) Field of Classification Search
CPC ......... A61B 50/24; A61B 50/26; A61B 90/25; A61B 90/50; A61B 2090/5025; A61B 2090/504; G02B 7/001; G02B 21/00–368; F16M 11/06; F16M 11/08; F16M 11/10; F16M 11/12; F16M 11/121; F16M 11/18
USPC .................................. 359/368–398
See application file for complete search history.

(56) References Cited

U.S. PATENT DOCUMENTS

| | | | | |
|---|---|---|---|---|
| 8,830,572 B2 * | 9/2014 | Graber | ................. | G02B 7/001 |
| | | | | 248/123.11 |
| 10,288,859 B2 * | 5/2019 | Nakamura | ............. | A61B 90/20 |
| 2005/0247831 A1 | 11/2005 | Nakamura | | |
| 2018/0100998 A1 * | 4/2018 | Tamura | ................. | A61B 90/20 |

FOREIGN PATENT DOCUMENTS

JP 4504081 7/2010

* cited by examiner

*Primary Examiner* — Ryan S Dunning
(74) *Attorney, Agent, or Firm* — Greenblum & Bernstein, P.L.C.

(57) ABSTRACT

A surgical microscope system includes a surgical microscope. When an additional unit is added to the microscope, the center of gravity of the microscope upwardly changes. In this case, an extension of a vertical-slider plate is joined with an upper joint location of a horizontal-slider plate, to raise a vertical slider together with a rotary shaft relative to the microscope, so that a weight balance of the microscope can be established only by sliding the vertical slider within its slidable range.

2 Claims, 7 Drawing Sheets

SURGICAL MICROSCOPE SYSTEM HAVING HORIZONTAL AND VERTICAL SLIDERS

BACKGROUND OF THE INVENTION

1. Field of the Invention

The present invention relates to a surgical microscope system, and particularly, to a surgical microscope system that supports, through vertical and horizontal sliders, a surgical microscope at a front end of a stand.

2. Description of Related Art

A surgical microscope system used for neurosurgery and the like includes a surgical microscope and a stand that supports the surgical microscope. The surgical microscope has a microscope body, an eyepiece unit for a main doctor arranged on a front side of the microscope body, and a light intake arranged on each of left and right side faces of the microscope body. To the light intake, an optical attachment such as an assistant scope, a camera, or the like is attached if required.

To one side face of the microscope body, a horizontal slider is arranged along a front-back direction of the microscope body. The horizontal slider has a horizontal-slider plate that is movable in a length direction of the horizontal slider. The horizontal slider is combined with a vertical slider that is in an upright state and is constituted like the horizontal slider. The vertical slider has a vertical-slider plate that is movable in a length direction of the vertical slider. The vertical-slider plate is joined with the horizontal-slider plate so that the vertical and horizontal sliders are combined together into a cross shape.

The surgical microscope with the combined horizontal and vertical sliders is supported with the stand and is suspended therefrom at an optional aerial position. The stand has a horizontally extending support arm whose front end has a downwardly extending suspension arm. A lower end of the suspension arm has a rotary shaft. To the rotary shaft, a face of the vertical slider opposing the vertical-slider plate is attached to thereby suspend the surgical microscope from the stand.

In a state that the surgical microscope is supported by the stand, an optical attachment such as an assistant scope, a camera, or the like is attached to the microscope body. This may change a gravity center of the surgical microscope. In this case, a position of the surgical microscope relative to the lower end of the suspension arm is adjusted through the horizontal and vertical sliders in the front-back and vertical directions, to balance the weight of the surgical microscope around the rotary shaft at the lower end of the suspension arm. A related art is disclosed in, for example, Japanese Patent Publication No. 4504081.

SUMMARY OF THE INVENTION

According to the related art, a change in the gravity center of the surgical microscope caused by attaching an optical attachment to the surgical microscope is dealt with a positional adjustment of the horizontal and vertical sliders. There is a recently proposed surgical microscope that has a microscope body dividable into upper and lower bodies between which an additional unit is installable. The additional unit provides the surgical microscope with an additional optical function such as a fluorescent function and a spectral function, to make the surgical microscope highly functional.

Adding the additional unit, however, increases the height of the surgical microscope to greatly change the gravity center thereof in the vertical direction. Then, a slidable range of the vertical slider will be insufficient to completely balance the weight of the surgical microscope around the rotary shaft.

In consideration of such a problem of the related art, the present invention provides a surgical microscope system capable of, even if an additional unit is added to a microscope body, easily balancing the weight of a surgical microscope around a rotary shaft.

According to an aspect of the present invention, the surgical microscope system includes a surgical microscope supported with a stand and including a microscope body, an eyepiece unit for a main doctor arranged on a front side of the microscope body, and a light intake arranged on each of left and right side faces of the microscope body, the microscope body being configured to be dividable into upper and lower bodies, and if required, to receive between the upper and lower bodies an additional unit that has side faces continuous to the microscope body and a predetermined height. The system also includes a horizontal slider fixed to one of left and right side faces of the lower body, the horizontal slider extending along a front-back direction of the microscope body and having a horizontal-slider plate that is movable in a length direction of the horizontal slider, and a vertical slider set in an upright state and having a vertical-slider plate that is movable in a length direction of the vertical slider and is joined with the horizontal-slider plate. A face of the vertical slider opposing the vertical-slider plate is rotatably attached to a rotary shaft that is arranged at a lower end of a suspension arm arranged at a front end of a support arm of the stand. An extension is formed on the vertical-slider plate so as to protrude from the vertical slider in one of front and back directions. Upper and lower joint locations are defined at upper and lower different height positions, respectively, on the horizontal-slider plate, each of the upper and lower joint locations being configured to join with the extension of the vertical-slider plate so that, if the additional unit is not set between the upper and lower bodies, the extension is joined with the lower joint location, and if the additional unit is set between the upper and lower bodies, the extension is joined with the upper joint location.

DESCRIPTION OF PREFERRED EMBODIMENTS

A surgical microscope system according to an embodiment of the present invention will be explained with reference to FIGS. 1 to 8.

Figure 1:
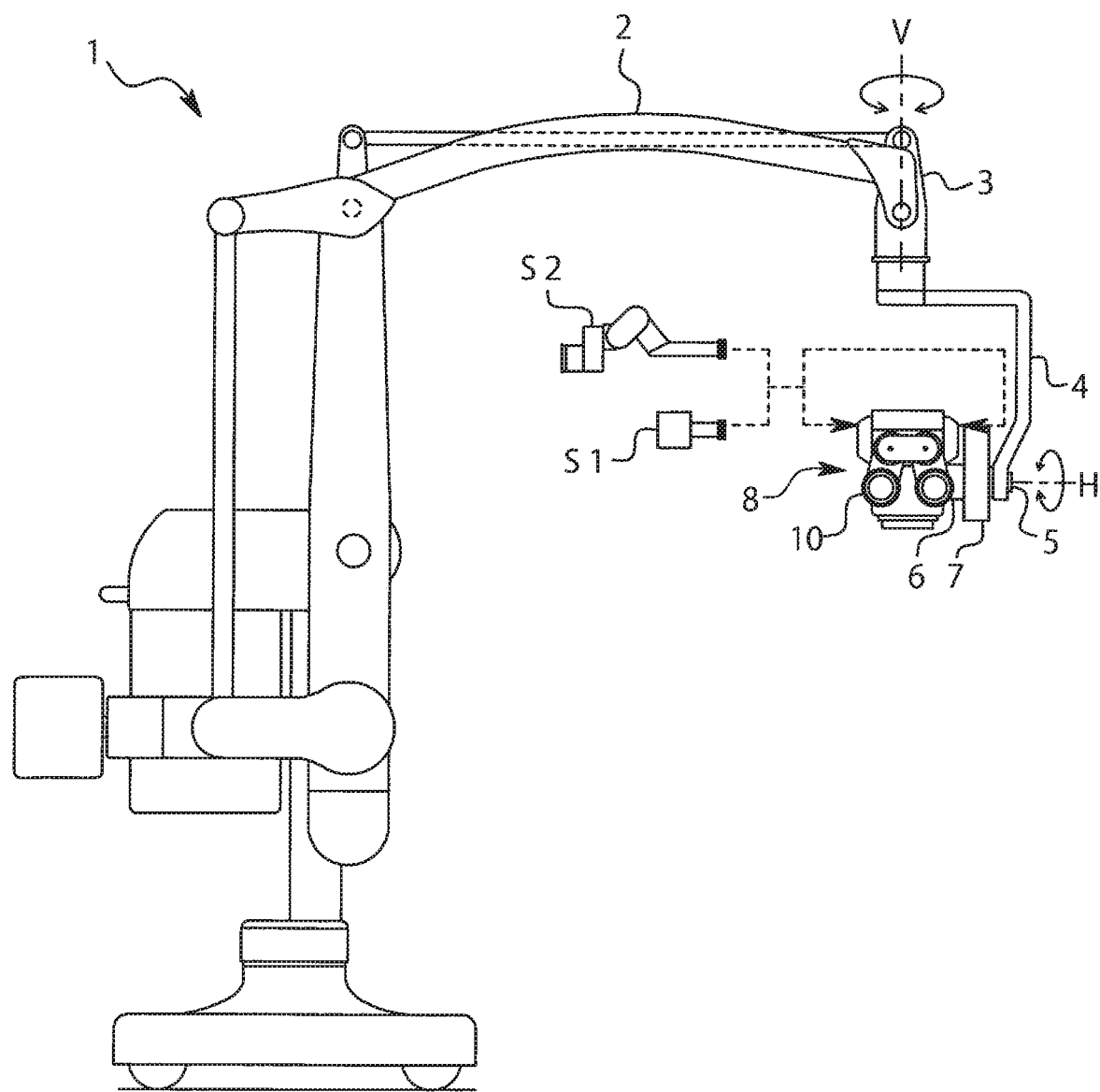
FIG. 1 is a side view illustrating a surgical microscope system according to an embodiment of the present invention.
Figure 2:
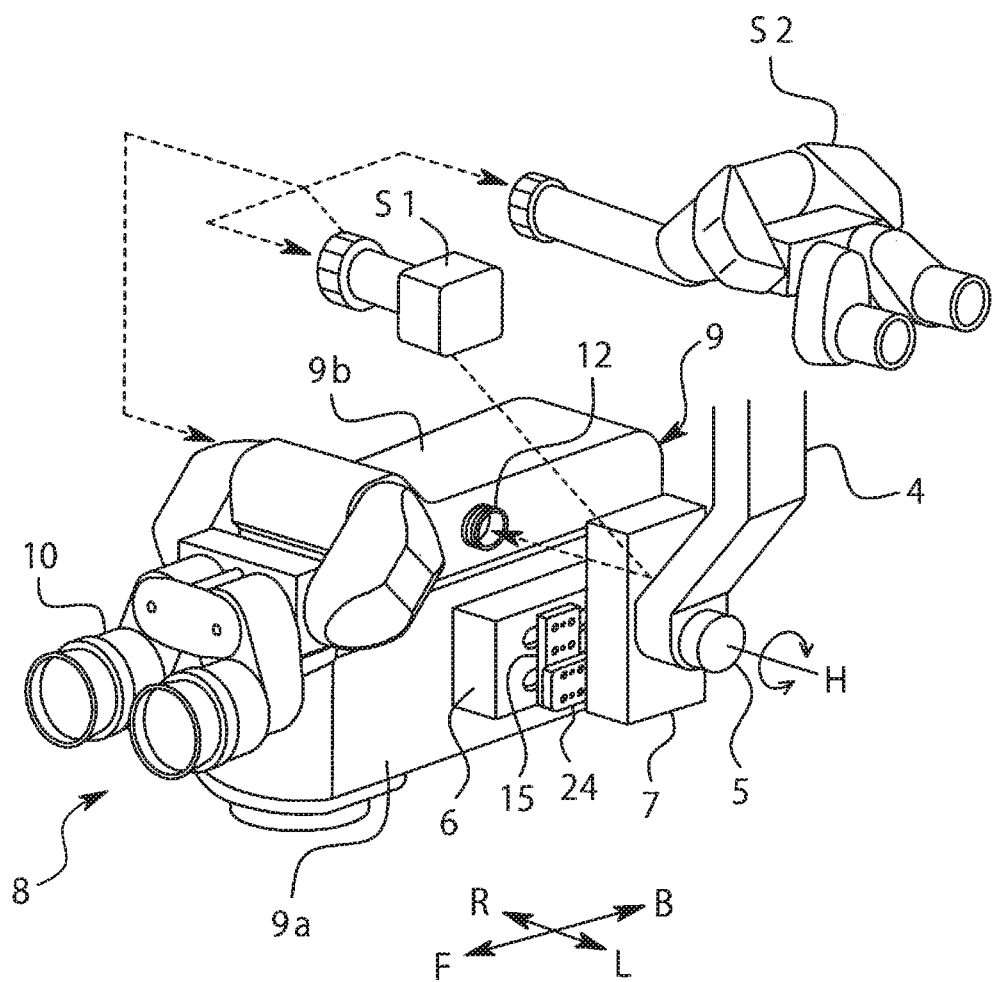
FIG. 2 is a perspective view illustrating a surgical microscope supported with a suspension arm in the surgical microscope system.
Figure 3:
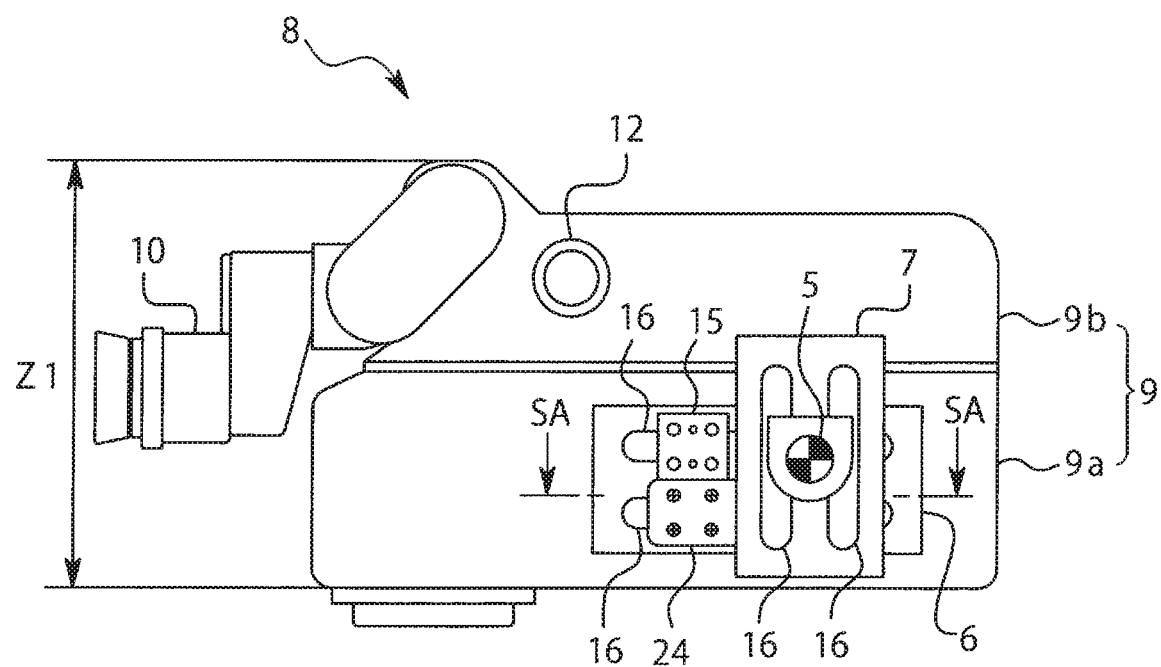
FIG. 3 is a side view illustrating the surgical microscope.
Figure 4:
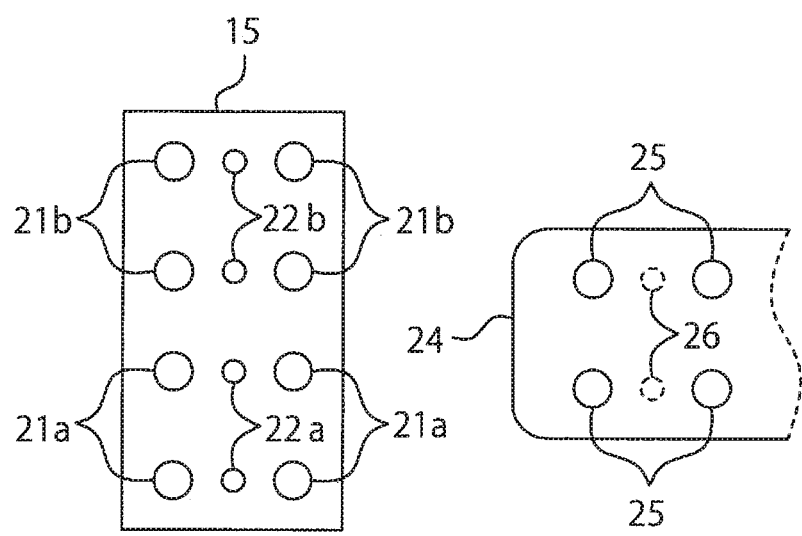
FIG. 4 is a side view illustrating a horizontal-slider plate and an extension of a vertical-slider plate.
Figure 5:
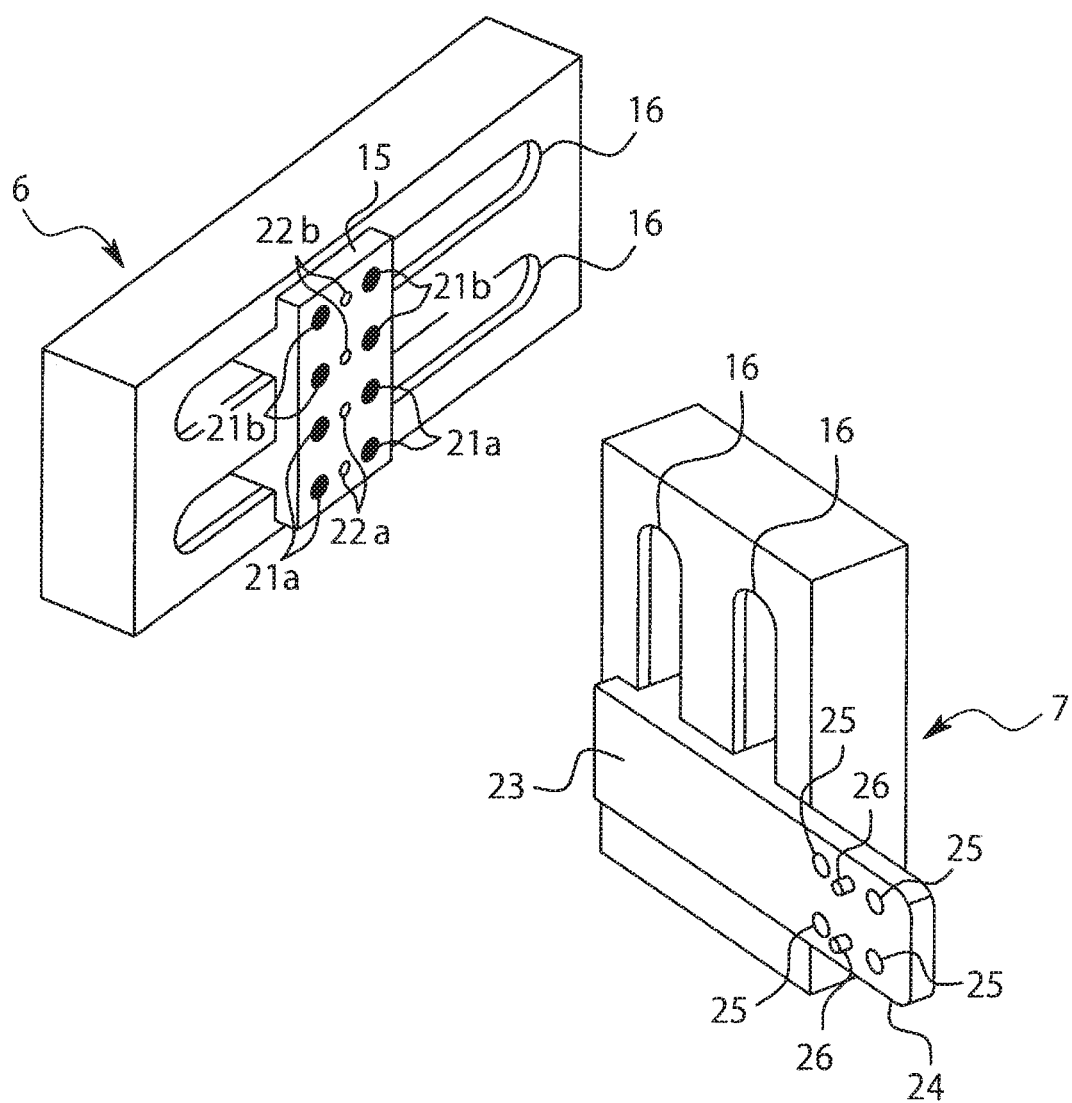
FIG. 5 is a perspective view illustrating a horizontal slider and a vertical slider.
Figure 6:
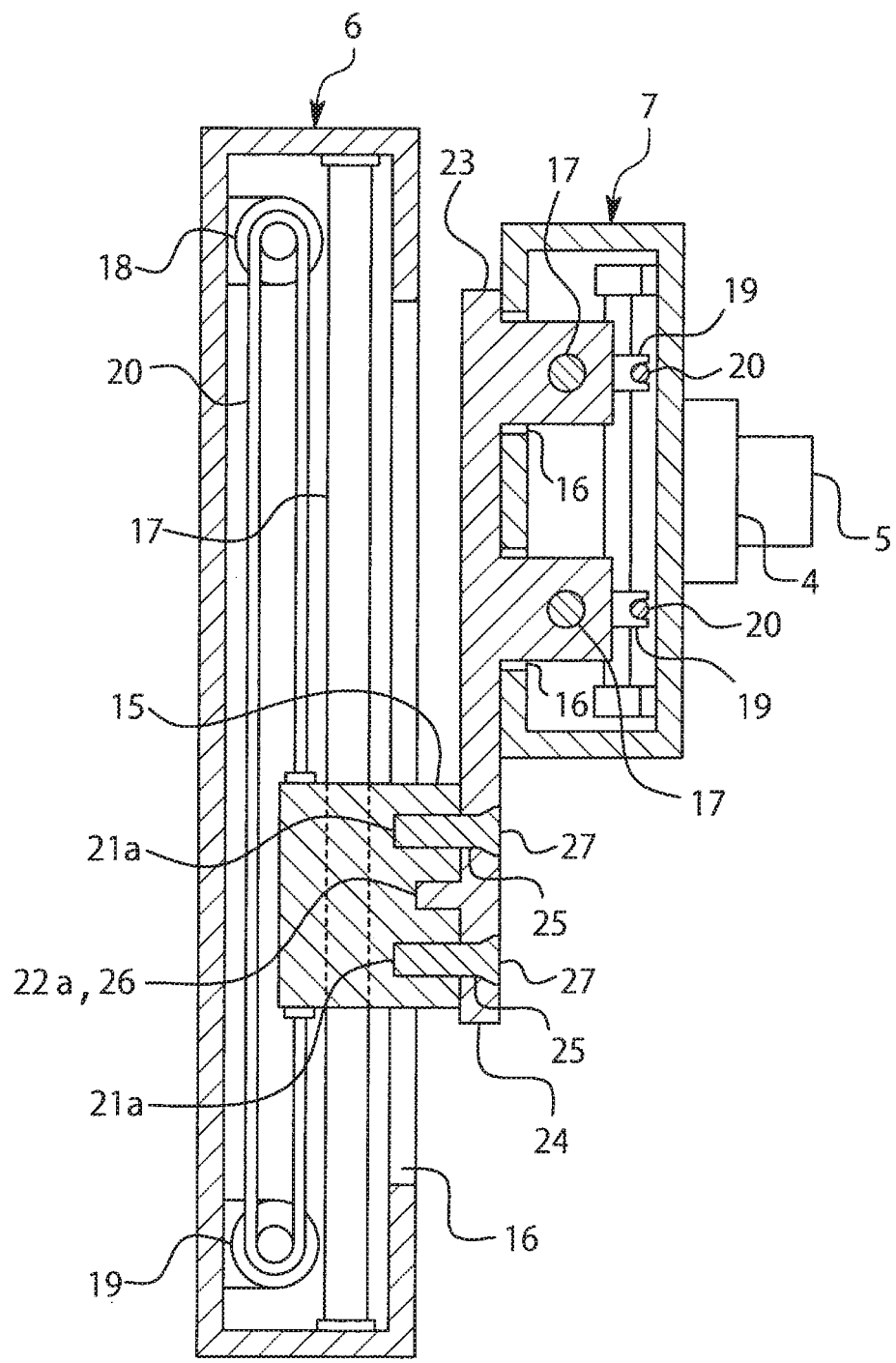
FIG. 6 is a sectional view taken along a line SA-SA of FIG. 3.

In the explanations above and below, front (F), back (B), left (L), and right (R) directions are as illustrated in FIG. 2. First, a stand 1 of the surgical microscope system will be explained.

The stand 1 has at an upper part thereof a horizontally extending support arm 2. A front end of the support arm 2 is provided with a front link 3. A lower end of the front link 3 is provided with a suspension arm 4 that is rotatable around a vertical axis V. A lower end of the suspension arm 4 has a rotary shaft 5 that is rotatable around a horizontal axis H. The rotary shaft 5 of the suspension arm 4 supports a surgical microscope 8 through a horizontal slider 6 and a vertical slider 7.

A structure of the surgical microscope 8 will be explained.

Figure 7:
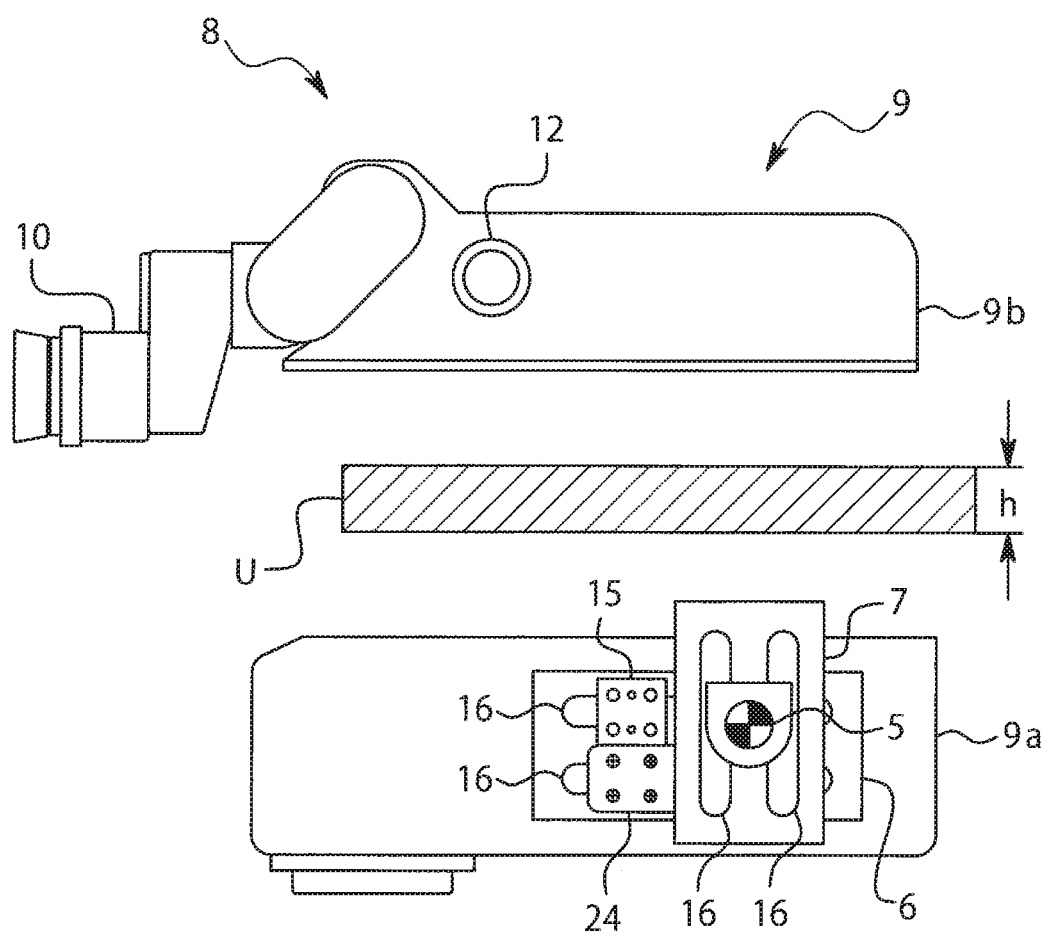
FIG. 7 is a side view illustrating a microscope body of the surgical microscope divided into upper and lower bodies.
Figure 8:
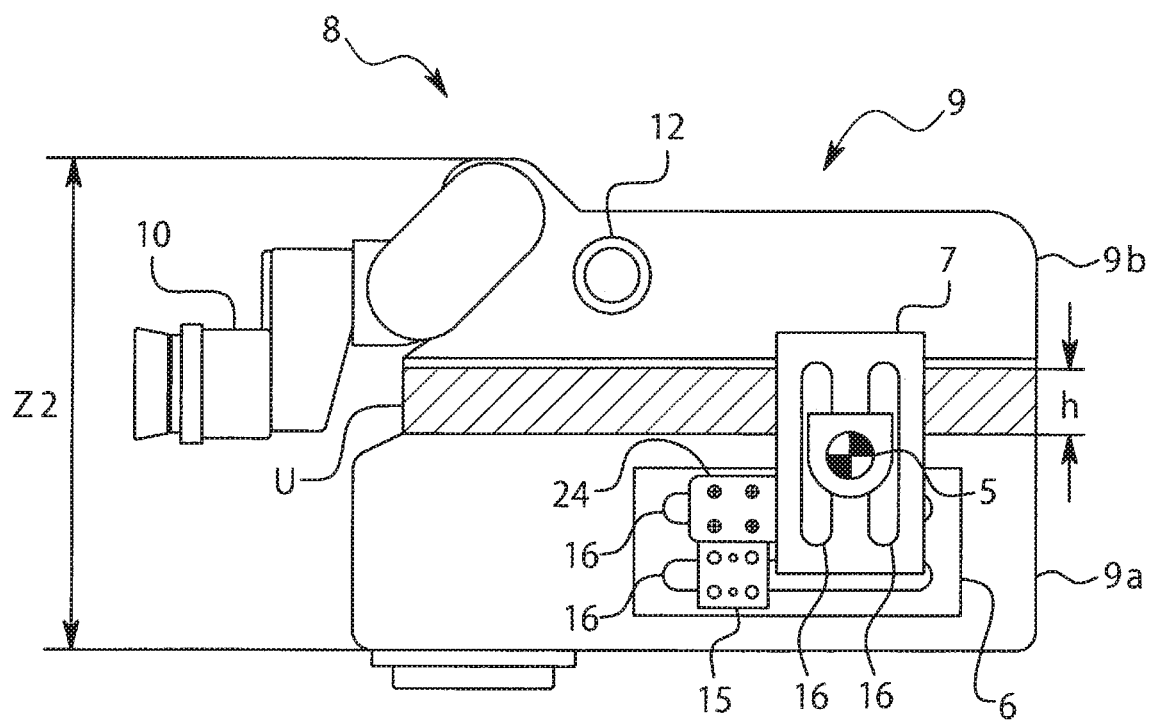
FIG. 8 is a side view illustrating the surgical microscope with an additional unit added between the upper and lower bodies.

The surgical microscope 8 basically has a microscope body 9 and an eyepiece unit 10 for a main doctor on a front side of the microscope body 9. The microscope body 9 is dividable into a lower body 9a and an upper body 9b. The lower body 9a and upper body 9b are usually integrated into one, and if required, an additional unit U is installed between the lower and upper bodies 9a and 9b as illustrated in FIGS. 7 and 8. The additional unit U has an additional optical function such as a phosphorescent function and a spectral function to functionally improve the surgical microscope 8.

The additional unit U has side faces continuous to the microscope body 9 and a predetermined height h. Accordingly, when combined with the additional unit U, the microscope body 9 increases its height from a non-combined height Z1 to a combined height Z2 (=Z1+h) that is higher than the height Z1 by the height h of the additional unit U.

The eyepiece unit 10 for a main doctor is arranged on a front side of the upper body 9b. On each of left and right side faces of the upper body 9b, a light intake 12 is formed. To the light intake 12, an optical attachment such as a camera S1 and an assistant scope S2 is attached as and when required.

The horizontal slider 6 has a horizontally extending cuboid shape and is provided with a horizontal-slider plate 15 that is movable in a length direction of the horizontal slider 6. In a state that the length direction of the horizontal slider 6 agrees with a front-back direction of the microscope body 9, a face of the horizontal slider 6 opposing the horizontal-slider plate 15 is fixed to a left side face of the lower body 9a.

The horizontal slider 6 has a pair of slits 16 along the length direction of the horizontal slider 6. Part of the horizontal-slider plate 15 enters through the slits 16 into the inside of the horizontal slider 6. Inside the horizontal slider 6, a pair of rails 17 is arranged along the slits 16. The rails 17 pass through the part of the horizontal-slider plate 15 inserted through the slits 16 so that the horizontal-slider plate 15 may stably slide along the rails 17 in the length direction of the horizontal slider 6.

Farther inside the horizontal slider 6, there are pulleys 18 and 19 around which a belt 20 is stretched. Each end of the belt 20 is connected to the part of the horizontal-slider plate 15 from the length direction of the horizontal slider 6. The pulleys 18 and 19 are driven by a motor (not illustrated) in forward and reverse directions. The rotating direction and amount of the pulleys 18 and 19 are controlled according to a balance detector (not illustrated). Rotating the pulleys 18 and 19 pulls, through the belt 20, the part of the horizontal-slider plate 15 in a given direction, thereby moving the plate 15 in the direction.

On a surface of the horizontal-slider plate 15, a lower joint location is defined where four threaded holes 21a and an upper and lower pair of locator holes 22a are formed. Above the lower joint location, an upper joint location is defined where four threaded holes 21b and an upper and lower pair of locator holes 22b are formed.

The vertical slider 7 is arranged along a vertical (up-down) direction, and similar to the horizontal slider 6, has a cuboid shape that is substantially vertically elongated. The vertical slider 7 has a vertical-slider plate 23 that is movable in a length direction of the vertical slider 7. A configuration of the vertical slider 7 is basically the same as that of the horizontal slider 6, and therefore, like structural parts are represented with like reference numerals to omit repetitive explanations.

What is structurally different from the horizontal slider 6 is that the vertical-slider plate 23 of the vertical slider 7 has an extension 24 that is integral with the vertical-slider plate 23 and is extended in the front direction. The extension 24 protrudes from the vertical slider 7 in the front direction and has four small holes 25 and an upper and lower pair of locator pins 26. The small holes 25 positionally agree with the threaded holes 21a or 21b and the locator pins 26 positionally agree with the locator holes 22a or 22b.

To combine the vertical slider 7 with the horizontal slider 6, the extension 24 is fitted to the lower joint location 21a or the upper joint location 21b of the horizontal-slider plate 15. As an example, a normal state in which the additional unit U is not added and the extension 24 is attached to the lower joint location 21a will be explained. The locator pins 26 of the extension 24 are fitted into the lower locator holes 22a of the horizontal-slider plate 15. With this, the extension 24 is correctly set at a proper joint location, i.e., the lower joint location 21a, and therefore, the four threaded holes 21a and the four small holes 25 agree with each other. In this state, long screws 27 are inserted through the small holes 25 and front ends of the screws 27 are screwed into the threaded holes 21a. As a result, the extension 24 is fixed to the lower joint location 21a of the horizontal-slider plate 15 and the vertical slider 7 is combined with the horizontal slider 6.

In the combined state, a face of the vertical slider 7 opposing the vertical-slider plate 23 is attached to the rotary shaft 5 that is arranged at the lower end of the suspension arm 4 of the stand 1. With this, the lower end of the suspension arm 4 supports, through the horizontal slider 6 and vertical slider 7, the surgical microscope 8.

The rotary shaft 5 becomes freely rotatable only when a clutch (not illustrated) is released. At the time of releasing the clutch, if the gravity center of the surgical microscope 8 disagrees with the rotary shaft 5, the balance detector (not illustrated) detects the disagreement and the gravity center of the surgical microscope 8 is adjusted to agree with the rotary shaft 5.

More precisely, the surgical microscope 8 in an unbalanced state is kept as it is and the horizontal-slider plate 15 is moved and slid to establish a weight balanced state in the front-back direction. Thereafter, the surgical microscope 8 is turned by 90 degrees into a vertical state, and in this state, the vertical-slider plate 23 is moved (in a horizontal direction in this state) to establish a weight balanced state in the front-back direct ion. Then, the surgical microscope 8 is returned to an original state. At this moment, the surgical microscope 8 is weight-balanced in orthogonal two directions. Namely, the weight balance of the surgical microscope 8 around the rotary shaft 5 is established, and therefore, the gravity center of the surgical microscope 8 completely agrees with the rotary shaft 5. Even if the main doctor releases the clutch of the rotary shaft 5 during operation to turn the surgical microscope 8 in an optional direction, the surgical microscope 8 will maintain the turned position.

The above-mentioned balancing adjustment is carried out after a required optical attachment is attached to the light intake 12 of the surgical microscope 8. Namely, attaching the required optical attachment to the surgical microscope 8 changes the gravity center of the surgical microscope 8 depending on the kind of the optical attachment, and therefore, the balancing adjustment must be carried out on a final configuration after the required optical attachment is added to the surgical microscope 8.

A change in the gravity center of the surgical microscope 8 caused by attaching only the camera S1 or the assistant scope S2 to the light intake 12 of the microscope body 9 may be coped with within slidable ranges of the horizontal and vertical sliders 6 and 7. Namely, by adjusting the sliders 6 and 7 within their slidable ranges, the weight balanced state of the surgical microscope 8 around the rotary shaft 5 will be established. However, a large change in the gravity center of the surgical microscope 8 that may occur when the additional unit U is added between the lower and upper bodies 9a and 9b of the surgical microscope 8 to cause the large height Z2 of the surgical microscope 8 will not be coped with only by adjusting, in particular, the vertical slider 7 within its slidable range.

In such a case, the joint location of the extension 24 of the vertical-slider plate 23 on the horizontal-slider plate 15 is changed from the lower joint location 21a to the upper joint location 21b. The jointing technique is the same as that to the lower joint location 21a. With this, the position of the vertical slider 7 relative to the surgical microscope 8 rises together with the rotary shaft 5 to cancel, to some extent, the upward change in the gravity center of the surgical microscope 8 caused by the addition of the additional unit U. Accordingly, sliding the vertical slider 7 within the slidable range thereof will establish a weight balanced state of the surgical microscope 8 around the rotary shaft 5 in the up-down direction.

In the above-mentioned embodiment, the lower joint location 21a and upper joint location 21b are clearly separated from each other. It is possible to partly overlap the upper and lower joint locations 21a and 21b.

According to the embodiment, the extension 24 protrudes from the vertical slider 7 in the front direction. Instead, the extension may protrude in the back direction. Any direction is allowed if a combined part between the extension 24 and the horizontal-slider plate 15 is not hidden behind the vertical slider 7.

In summary, the surgical microscope system according to an aspect of the present invention forms an extension to a vertical-slider plate of a vertical slider, defines lower and upper joint locations on a horizontal-slider plate of a horizontal slider, joins the extension to the lower joint location when no additional unit is added to a surgical microscope, and when an additional unit is added to the surgical microscope, to the upper joint location. When the extension is joined with the upper joint location, a position of the vertical slider relative to the surgical microscope rises together with a rotary shaft to which the vertical slider is attached. As a result, an upward change in a gravity center of the surgical microscope caused by the addition of the additional unit is cancelled to some extent, so that sliding the vertical slider within its slidable range can establish an up-down directional weight balanced state of the surgical microscope around the rotary shaft.

Further, fitting locator pins of the extension into locator holes of the horizontal-slider plate can set the extension at a correct joint position with respect to the corresponding lower or upper joint location on the horizontal-slider plate. This makes it easy to carry out jointing work of the extension and the joint location of the horizontal-slider plate with screws.

This patent application claims the benefit of priority under 35 U.S.C. 119(a) to Japanese Patent Application No. 2017-208797 filed on Oct. 30, 2017 whose disclosed contents are cited herein.

What is claimed is:

1. A surgical microscope system comprising:
a surgical microscope supported with a stand and including a microscope body, an eyepiece for a user arranged on a front side of the microscope body, and a light intake arranged on each of left and right side faces of the microscope body, the microscope body being configured to be dividable into upper and lower bodies, and configured to receive between the upper and lower bodies an additional optical structure having side faces continuous to the microscope body and a predetermined height;
a horizontal slider fixed relative to one of left and right side faces of the lower body, the horizontal slider extending along a front-back direction of the microscope body and having a horizontal-slider plate that is movable in a length direction of the horizontal slider; and
a vertical slider extending along an up-down direction of the microscope body and having a vertical-slider plate that is movable in a length direction of the vertical slider and is joined with the horizontal-slider plate, wherein:
a face of the vertical slider opposing the vertical-slider plate is rotatably attached to a rotary shaft that is arranged at a lower end of a suspension arm arranged at a front end of a support arm of the stand;
an extension is formed on the vertical-slider plate so as to protrude from the vertical slider in one of front and back directions; and
upper and lower joint locations are defined at upper and lower different height positions, respectively, on the horizontal-slider plate, each of the upper and lower joint locations being configured to join with the extension of the vertical-slider plate, wherein in a case where the additional optical structure is not set between the upper and lower bodies, the extension is joined with the lower joint location, and in a case where the additional optical structure is set between the upper and lower bodies, the extension is joined with the upper joint location.

2. The surgical microscope system of claim 1, wherein:
the upper and lower joint locations of the horizontal-slider plate and the extension of the vertical-slider plate are configured to be fixed to each other with screws; and
a plurality of locator holes are formed on either the joint locations or the extension, and a plurality of locator pins are formed on the other of either the joint locations or the extension, the locator pins being fitted into the locator holes to correctly position the extension at an intended one of the upper and lower joint locations on the horizontal-slider plate.

\* \* \* \* \*